United States Patent [19]

Nagashima et al.

[11] Patent Number: 5,663,502

[45] Date of Patent: Sep. 2, 1997

[54] METHOD AND APPARATUS FOR MEASURING THICKNESS OF LAYER USING ACOUSTIC WAVES

[75] Inventors: Yoshiaki Nagashima; Kenichi Fujiwara, both of Hitachi; Masao Sato, Kitaibaraki; Fuminobu Takahashi, Hitachinaka; Masahiro Koike, Hitachi; Hajime Umehara, Hitachinaka; Yoshihiro Michiguchi, Ibaraki-ken, all of Japan

[73] Assignees: Hitachi, Ltd., Tokyo; Hitachi Nuclear Engineering Co., Ltd., Hitachi, both of Japan

[21] Appl. No.: 544,932

[22] Filed: Oct. 18, 1995

[30] Foreign Application Priority Data

Oct. 18, 1994 [JP] Japan ............... 6-251784

[51] Int. Cl.$^6$ ........................... G01N 29/08; G01N 29/10
[52] U.S. Cl. ................... 73/599; 73/602; 364/507
[58] Field of Search ................ 73/588, 597, 579, 73/599, 602, 606, 609, 620, 628, 627, 629; 128/660.06, 660.01; 364/507, 563

[56] References Cited

U.S. PATENT DOCUMENTS

| | | | |
|---|---|---|---|
| 4,305,294 | 12/1981 | Vasile et al. | 73/579 |
| 4,452,082 | 6/1984 | Miwa | 73/599 |
| 4,539,847 | 9/1985 | Paap | 73/579 |
| 4,625,556 | 12/1986 | Sukahara et al. | 73/602 |
| 4,646,748 | 3/1987 | Fujii et al. | 73/599 |
| 4,648,276 | 3/1987 | Klepper et al. | 73/599 |
| 5,271,274 | 12/1993 | Khuri-Yakub et al. | 73/597 |
| 5,305,239 | 4/1994 | Kinra | 73/602 |
| 5,351,544 | 10/1994 | Endo et al. | 73/588 |
| 5,408,881 | 4/1995 | Piché et al. | 73/588 |
| 5,426,979 | 6/1995 | Kantorovich et al. | 73/628 |

*Primary Examiner*—Hezron E. Williams
*Assistant Examiner*—Rose M. Miller
*Attorney, Agent, or Firm*—Antonelli, Terry, Stout & Kraus, LLP.

[57] ABSTRACT

Ultrasonic waves from a transmit device are transmitted to an object subject to measurement. A surface reflected wave propagated in a contact medium and reflected at the surface of a tube and bottom surface reflected waves passing through an oxidation layer on the tube and reflected at the inner surface of the tube are convened into electric signals. A feature extracting part 5, in consideration of a correlation relationship of energy with respect to the frequency of a received signal, based on the received signal of ultrasonic waves converted to electric signals, extracts a signal feature data determined beforehand which has a strong correlation relationship with the thickness of a measured part. Based on the extracted signal feature data, a thickness conversion part references a relationship storage part which has stored therein beforehand a function that shows a relationship between the signal feature data and the thickness of the oxidation layer, and obtains the thickness of the oxidation layer.

8 Claims, 17 Drawing Sheets

METHOD AND APPARATUS FOR MEASURING THICKNESS OF LAYER USING ACOUSTIC WAVES

FIELD OF THE INVENTION

The present invention is related to an apparatus that measures the thickness of an object, and is especially related to a thickness measuring apparatus that suitably measures thin coatings and such formed on the surface of an object.

BACKGROUND OF THE INVENTION

In the case of measuring the thickness of a coating by using ultrasonic waves, a method is known in which ultrasonic waves are transmitted to an object having a coating formed on the surface and the thickness is determined from the difference in the propagation times or sound velocities of reflected waves between the top and bottom surfaces of the coating. However, the above method cannot be utilized when the reflected waves of sufficient strength cannot be had from the boundary surfaces because there is only a small change in an acoustic characteristic between the coating and the base metal or when the difference of the propagation times of reflected waves cannot be made distinct because the coating layer is too thin.

In contrast, when the attenuation of ultrasonic waves between the coating layer and the base metal differs, the following methods are available. First, there is a method disclosed in JP-A-6-18487. In this method, with regard to a cylindrical object having a hardened layer on the outer part, ultrasonic waves are transmitted to the cylindrical object in the chord direction, transmitted ultrasonic waves in the chord direction of said object are received, a frequency spectrum of the transmitted ultrasonic waves at each position of the chord is obtained by scanning the position of the chord in the diameter direction, and the depth of said hardened layer is determined based on the change in these spectral frequency patterns. Second, according to "Acoustic Properties of Plasma-sprayed Coatings and their Applications to Non-destructive Evaluation," *Thin Solid Films* (Vol. 83, No. 3, Pages 311-324, 1981), a coating thickness is determined by measuring the attenuation of ultrasonic waves transmitted through plasma-sprayed coatings.

In JP-A-6-18487 referred to above, since a change in the received waves is observed by changing the position of a chord, which is measured by scanning the position of a probe that transmits and receives ultrasonic waves, and by propagating ultrasonic waves, which go from a transmitter to a receiver, through a coating layer under different conditions, the use of this method is limited to a case for a chord direction of a cylindrical material. In contrast, since the method of the *Thin Solid Films* reference referred to above obtains beforehand a relationship between amplitudes of transmitted waves and coating layer thicknesses and converts amplitude into thickness based on this relationship, it would be sufficient to obtain ultrasonic waves transmitted through the coating layer; and there would be little limitations on the object to be measured. However, when there are changes in the amplitudes of transmitted waves by causes other than due to thickness and when the amount of contribution by these causes is unknown, the use of this method will not suitable. The reasons can be found in the following cases. First, there is a case of an ultrasound transmit/receive apparatus not directly contacting the object to be measured. In this instance, ultrasonic waves are transmitted to the object via a medium used to establish contact with the object (called a contact medium), but the acoustic characteristic in this case induces change in the transmission rate. Second, there is a case of an ultrasound transmit/receive apparatus being placed only on one side of the object. In this instance, ultrasonic waves are reflected at the boundary between the reflection surface of the object and the contact medium, but the reflection rate is changed because of the acoustic characteristic in this case. In both of these cases, there are changes in the apparent attenuation because of the changes in the energy distribution at the boundary surface between the object and the contact medium. This apparent attenuation is different from the attenuation that depends on the thickness of the coating layer of the object. If the acoustic characteristic of the contact medium is known, these two different attenuations can be separated, but if not known, they cannot be distinguished, and consequently, a large estimation error can result because of the changes in the apparent attenuation.

SUMMARY OF THE INVENTION

The object of the present invention is to provide a thickness measuring method and an apparatus thereof that measure the thickness of an object without being affected by transmission and reflection rates even when a contact medium, which is a contacting material that encompasses the object, used during measurement is different or unknown with respect to the contact medium used at the time to obtain a relationship between the thickness of the object and received wave characteristics.

In order to realize the above object, a thickness measuring method of the present invention provides a thickness measuring method for transmitting ultrasonic waves to an object to be measured, receiving an acoustic receive signal emitted from the object, and measuring the thickness of a subject-to-measurement domain of the object based on the acoustic receive signal, comprising the steps of transmitting ultrasonic waves to a plurality of test objects each having a domain, which corresponds to the subject-to-measurement domain of the object, of a known but different thickness; receiving acoustic receive signals emitted from the test objects; and obtaining beforehand a signal feature data that has a strong correlation with the thickness of the subject-to-measurement domain, based on a correlation relationship of energy with respect to the frequency of the acoustic receive signal, and also determining a thickness function that defines a relationship between the signal feature data and the domain of each of the test objects; obtaining a measurement data that corresponds to the signal feature data when measuring the thickness of the subject-to-measurement domain of the object by receiving the acoustic receive signal from the object; and determining the thickness of the subject-to-measurement domain based on the measurement data and the thickness function.

In this instance, the signal feature data may be a center-of-frequency derived from a frequency spectrum of the acoustic receive signal. Furthermore, instead of this, the signal feature data may be a data that describes an attenuation feature among a plurality of frequency spectra of acoustic receive signals traveling different distances of propagation in the subject-to-measurement domain. In this instance, it is desirable to have at least one of the coefficients of an approximated equation approximating said attenuation feature by a curve be the data that indicates the attenuation feature.

Further, a thickness measuring apparatus of the present invention provides acoustic signal transmit/receive means for transmitting ultrasonic waves to an object and receiving an acoustic signal emitted from the object when measuring the thickness of a subject-to-measurement domain of the object; feature extracting means for obtaining beforehand a signal feature data that has a strong correlation with the thickness of the subject-to-measurement domain, based on a correlation relationship of energy with respect to the frequency of the acoustic signal received by the acoustic signal transmit/receive means; relationship storage means for storing a thickness function that defines a relationship between the signal feature data and the thickness of the subject-to-measurement domain; thickness conversion means for converting a measurement data, which corresponds to the signal feature data obtained beforehand by the feature extracting means, into the thickness of the subject-to-measurement domain by referencing the thickness function stored in the relationship storage means; and output means for yielding conversion results of the thickness conversion means.

In this instance, the feature extracting means comprises waveform excising means for excising a processing waveform from the acoustic signal received by the acoustic signal transmit/receive means; frequency spectrum calculation means for calculating a frequency spectrum of an excised waveform excised by the waveform excising means; and center-of-frequency calculation means for calculating a center-of-frequency of a frequency spectrum calculated from the frequency spectrum calculation means.

Alternatively, the feature extracting means comprises waveform excising means for excising a processing waveform from the acoustic signal received by the acoustic signal transmit/receive means; frequency spectrum calculation means for calculating a frequency spectrum of an excised waveform excised by the waveform excising means; attenuation calculation output means for yielding, as a signal feature data, at least one of the coefficients of an approximation equation approximating the attenuation feature by a curve.

Further, it is desirable to have the acoustic signal transmit/receive means comprise means for producing a shear wave in the subject-to-measurement domain; and means for receiving a shear wave that has propagated through the subject-to-measurement domain. Or instead of this, the acoustic signal transmit/receive means may comprise means for producing an acoustic surface wave in the subject-to-measurement domain; and means for receiving an acoustic surface wave that has propagated through the subject-to-measurement domain.

One embodiment of the invention will now be described by way of examples with references to the accompanying drawings.

DESCRIPTION OF THE PREFERRED EMBODIMENTS

Figure 1:
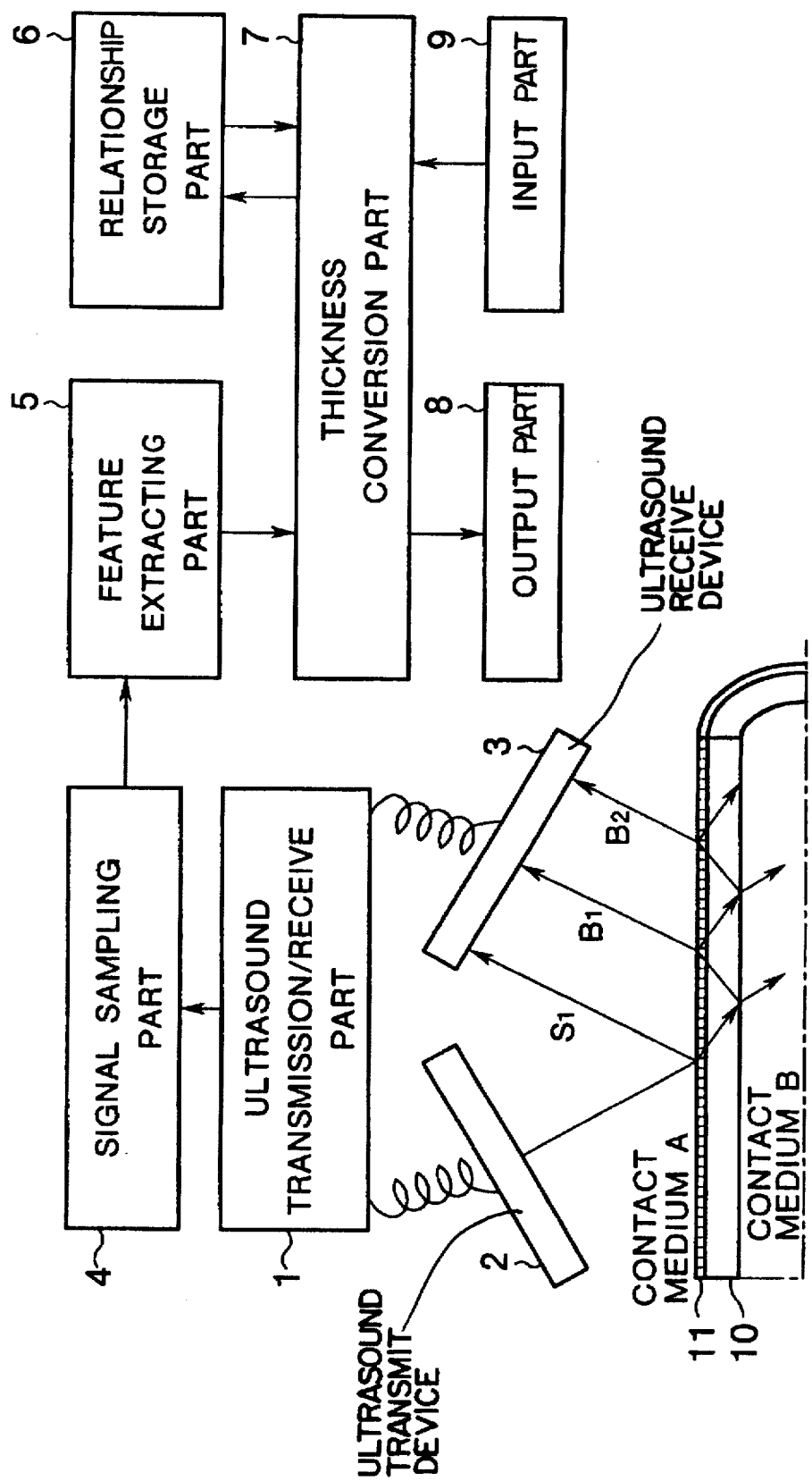
FIG. 1 shows a schematic drawing of one structural example of a thickness measuring apparatus of the present invention.

The present invention is explained below with reference to the drawing figures.

In FIG. 1, a schematic structure of the thickness measuring apparatus according to the present invention that measures the thickness of an oxidation layer formed on the surface of a tube as an object for measurement is shown. In accordance with the same figure, the measuring apparatus has an ultrasound transmit/receive part 1, an ultrasound transmit device 2, an ultrasound receive device 3, a signal sampling part 4, a feature extracting part 5, a relationship storage part 6, a thickness conversion part 7, an output part 8, and an input part 9.

With regard to FIG. 1, a tube 10 having an oxidation layer 11 on the surface, the ultrasound transmit device 2, and the ultrasound receive device 3 are all placed inside a contact medium A, which is a medium that surrounds the object under measurement. In this instance, the tube 10 is hollow, but its inside is assumed to be filled with a contact medium B (which can be different from the contact medium A). The ultrasound transmit device 2 generates ultrasonic waves via transmit pulses outputted from the ultrasound transmit/receive part 1.

The ultrasonic waves transmitted from the ultrasound transmit device 2 divide into reflected waves that are reflected at the surface of the tube 10 after propagating inside the contact medium A and refracted waves that are emitted into the tube 10. The refracted waves, in turn, divide into ultrasonic waves that refract at the inner surface of the tube 10 and propagate inside the contact medium B, and ultrasonic waves that reflect at the inner surface of the tube 10 and propagate in succession inside the tube 10. By the repetition of this phenomenon, ultrasonic waves are emitted into the inside of the contact medium A from the inside of the tube 10 at a time interval that depends on the wall thickness of the tube 10. That is, these waves that are emitted from the tube 10 are constituted by a surface reflected wave (S1), a reflected wave from the surface of the tube 10, and bottom surface reflected waves such as a 1st bottom echo (B1) reflected at the inner surface of the tube 10 and a 2nd bottom echo (B2); and are received by the ultrasound receive device 3.

The receive signals of the ultrasonic waves received by the ultrasound receive device 3 are converted into electric signals and amplified by the ultrasound transmit/receive part 1. The amplified receive signals are converted into digital signals by the signal sampling part 4, which is constituted by a digital oscilloscope and such, and stored.

The feature extracting part 5 receives the digitized receive signals stored in the signal sampling past 4 and extracts a signal feature data, which has a strong correlation with the thickness of the oxidation layer 11, the measuring point, in consideration of the correlation relationship of signal energy with respect to the frequency of the receive signals. This signal feature data is defined beforehand.

The thickness conversion part 7 receives a measurement data of the signal feature data extracted by the feature extracting part 5; references a thickness function, which shows the relationship between the signal feature data and the thickness of the oxidation layer 11 and is stored beforehand in a relationship storage part 6; and obtains the thickness of the oxidation layer 11 which corresponds to the measurement data in relation with the extracted signal feature data. The determined thickness of the oxidation layer 11 is outputted from the output part 8 constituted by a CRT, printer, and such.

The thickness function stored in the relationship storage part 6, which shows a relationship between the signal feature data and the thickness of the oxidation layer 11 with respect to a plurality of the tubes 10 that differ in oxidation layer thickness, is constructed for obtaining the signal feature data as described above by using the measuring apparatus as shown in FIG. 1. When constructing this thickness function at a time hereinafter called the relationship storage time, it is measured by other thickness measuring methods such as a destructive examination method or a non-destructive examination method. Then, the signal feature data and the function of the oxidation layer 11 derived by using the thickness measuring apparatus as shown in FIG. 1 are constructed beforehand and stored in the relationship storage part 6. In order to facilitate the construction of this thickness function, when the thickness of the oxidation layer 11 is already known, there is provided a function for inputting the thickness data of the oxidation layer 11 from an input part 9 constituted by a keyboard and such.

By using the apparatus of FIG. 1, since the received signal is converted into a frequency spectrum, an amplitude spectrum with respect to frequency can be obtained. Because of this, when there is a change in the spectrum distribution structure of the receive waves, depending on the thickness of the oxidation layer 11 in which ultrasonic waves have passed through, a measurement of the thickness becomes possible by evaluating the relative amplitudes. That is, by normalizing the frequency spectrum and by evaluating the amplitude distribution, the influence of apparent attenuation can be eliminated. In other words, even if there is an apparent attenuation that can influence the amplitudes of the received signal, the apparent attenuation that does not influence the relative amplitudes can be eliminated. For instance, when the contact medium B used at the time to obtain the relationship between the receive waves and the thickness of the oxidation layer 11 was gaseous but the contract medium B during actual measurement was liquid, the amplitude of the ultrasonic waves reflected at the bottom surface of the tube 10 would be reduced. However, even if this is the case, the spectrum distribution of the receive waves would be generally similar, and a measurement that does not produce a thickness estimation error would become possible.

Figure 2:
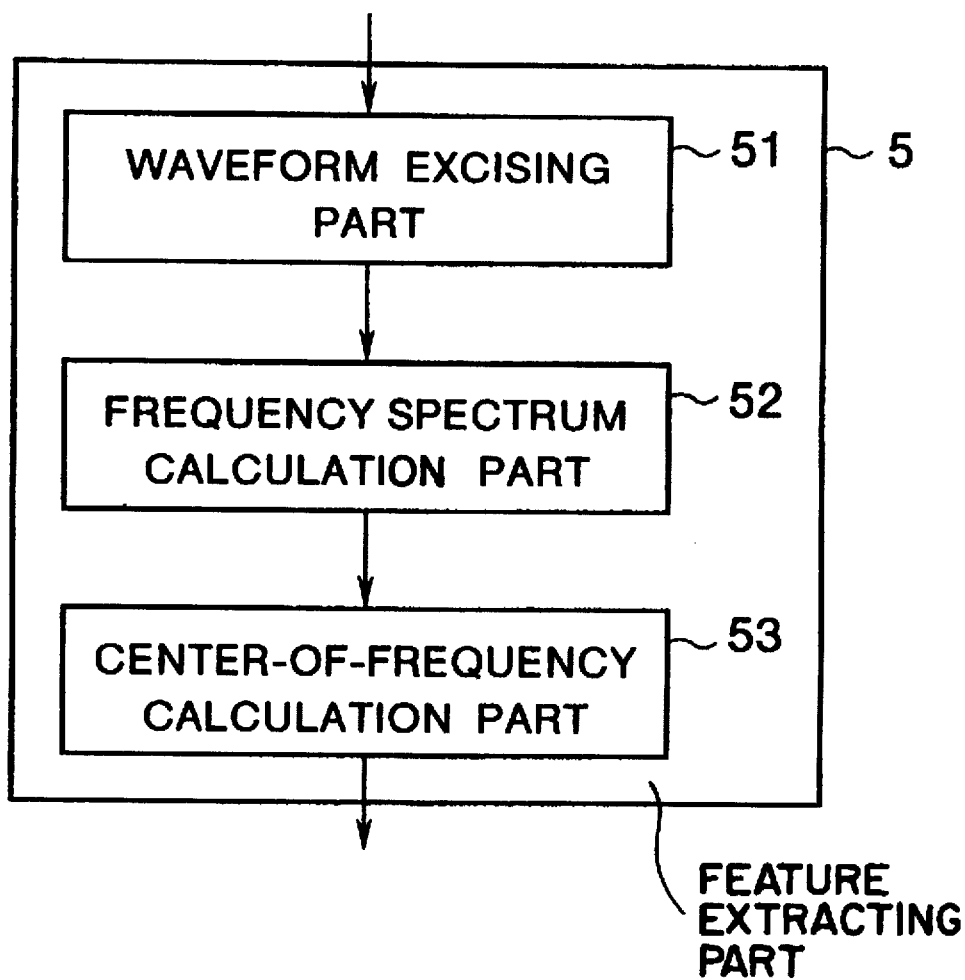
FIG. 2 shows a block diagram of one structural example of a signal feature extracting part of FIG. 1.

Next, a concrete structure example of the feature extracting part 5 with reference to FIG. 2 is explained. As shown in FIG. 2, the feature extracting part 5 has a waveform excising part 51, a frequency spectrum calculation part 52, and a center-of-frequency calculation part 53.

Figure 3:
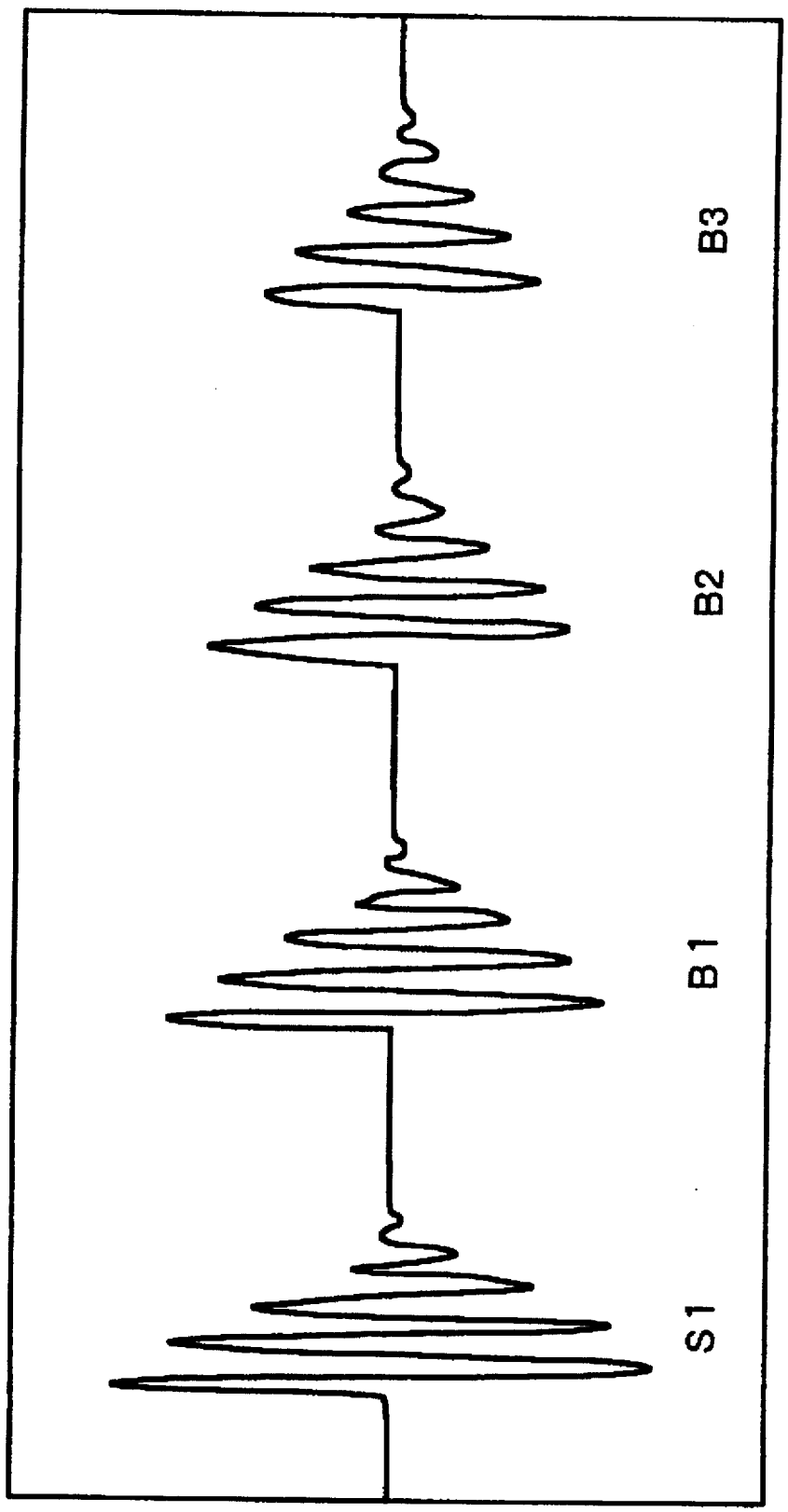
FIG. 3 is a descriptive diagram of reflection waves from a tube that is an object of measurement.

First, the waveform excising part 51 excises a waveform, subject to processing, after the conversion of the receive signals of the ultrasonic waves into digital signals by the signal sampling part 4 of FIG. 1. An excision method can be realized by having a fixed time window from the onset of the waveform. Also, an operator can set the time window directly. A waveform, subject to processing, such as a surface reflected echo (S1) and a bottom reflected echo Bi (i=1, 2, . . . , where i is a reflection number at the bottom surface of the object, subject to measurement) as indicated in FIG. 3, is a waveform that includes bottom surface reflected waves, which are influenced by the oxidation layer 11 formed on the surface of the tube 10. That is, a waveform after B1 can by itself be processed, or a plurality of waveforms all together can be processed, such as the waveform B1 and the waveform B2, or the waveform S1 and the waveform B1 and the waveform B2. Furthermore, a time range of choice for the bottom surface reflection wave can be the basis for processing. However, the time range must be the same for the relationship storage time and for the measurement time.

The excised waveform excised by the waveform excising part 51 is converted into a frequency spectrum via an FFT or such processing by the frequency spectrum calculation part 52. From this frequency spectrum, a center-of-frequency is calculated by the center-of-frequency calculation part 53. The center-of-frequency, fm, of the frequency spectrum is shown by Eq. (1) in which the frequency spectrum is g(f) and the frequency is f.

$$fm = \int (g(f) \cdot f) df / \int g(f) df \qquad (1)$$

The reason why this center-of-frequency is not influenced by the type of the contact medium B is that since transmission and refraction rates, which change when a different contact medium is used, do not depend on frequency (Ultrasound Technology Compendium, p. 18, formulas (1.1.48) and (1.1.49), published by Nikkan Kogyo Shinbunsha, Dec. 1, 1980), and since the spectrum g(f) is a product of a real coefficient p and g(f), p·g(f), they are cancelled out by the numerator and the denominator. Furthermore, since the center-of-frequency is an integration information, even if a small change is produced in the frequency spectrum by electric noise and such, the influence of this noise will not be significant. It should be noted that integration limits for determining fm are not specified here (they are determined by the frequency range specified by the FFT) but a certain interval may be specified for determining fm.

Figure 4:
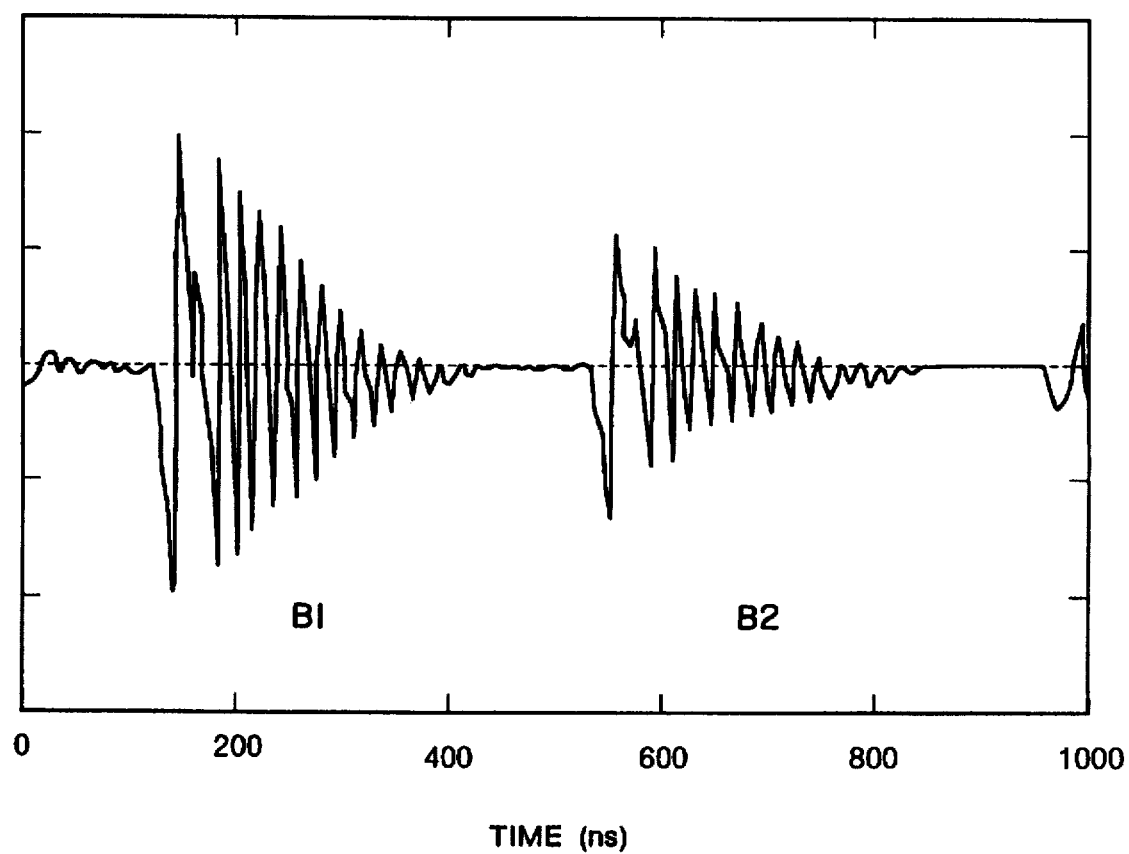
FIG. 4 is a descriptive diagram of bottom surface reflection waves from a tube that is an object of measurement.
Figure 5:
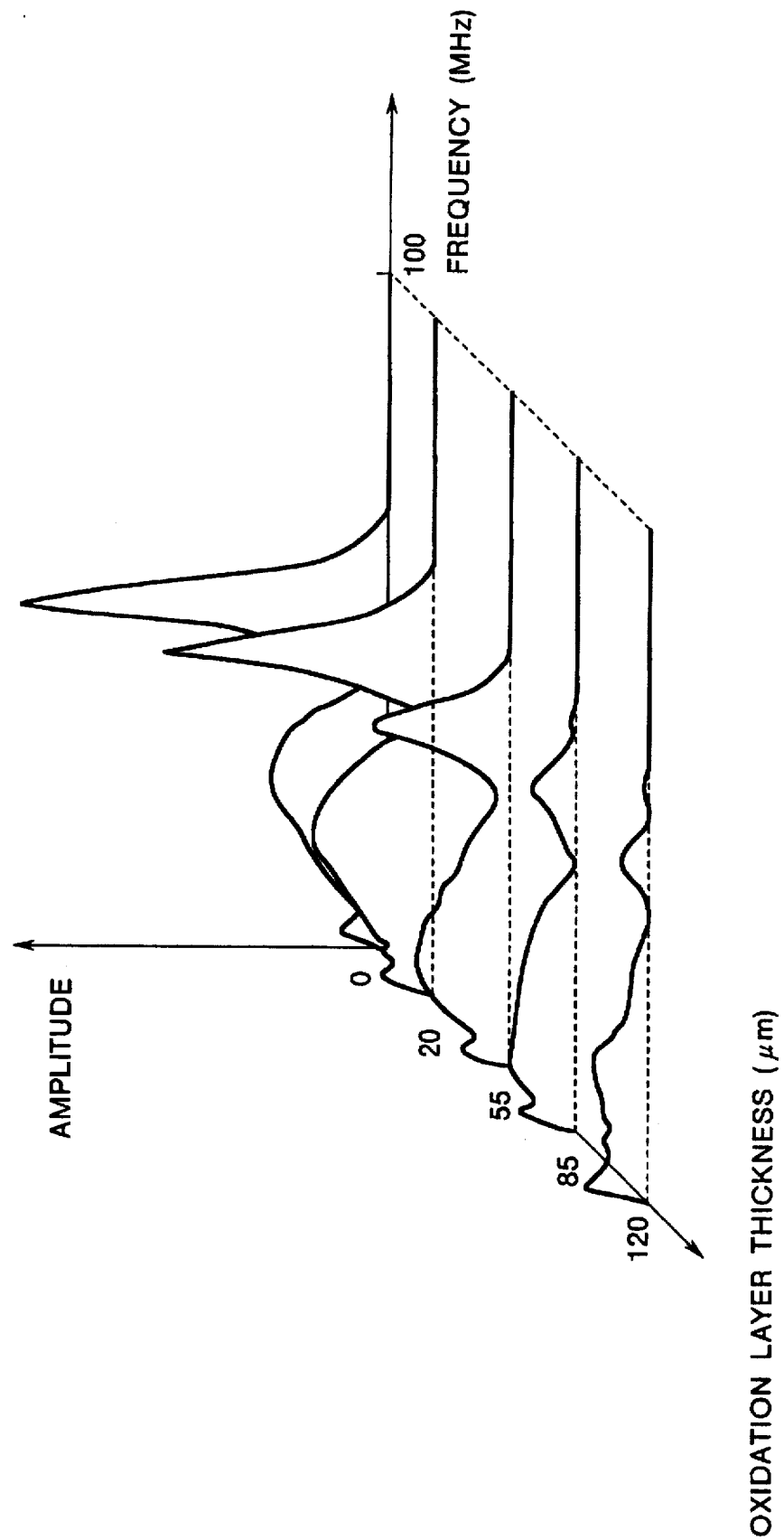
FIG. 5 is a descriptive diagram of changes of a frequency spectrum of reflection waves with respect to an oxidation layer thickness.

At this point, an experimental result conducted by the inventors in which the frequency spectrum is influenced by the oxidation layer 11 is presented. First, an experimental model having an oxidation layer that has the same characteristic as that of the tube 10 and the apparatus of FIG. 1 are prepared, and receive signals of a differing oxidation layer thickness are obtained. The first bottom surface echo and the second bottom surface echo with no oxidation layer are indicated in FIG. 4, and a frequency spectrum of the first bottom surface echo with respect to differing oxidation layer thicknesses is indicated in FIG. 5. From this figure, it can be seen that the amplitudes of the frequency spectrum grow smaller as the oxidation layer thickens. The reason for this is the large scattering attenuation attributed to gas cavities, cracks, grain boundaries, and organization boundaries. The scattering attenuation occurs because of nonuniformity of material and because ultrasonic waves are scattered at boundaries where acoustic characteristics change suddenly.

Additionally, as shown in FIG. 5, as the frequency increases, a reduction of amplitude influenced largely by the oxidation layer thickness is seen. When the wavelength of the ultrasonic waves are equivalent or larger than an air cavity or a grain, the phenomenon of differing degree of attenuation scattering is produced according to the wavelength. For example, the attenuation rate, $\alpha$, according to the scattering attenuation at the grain boundary can be theoretically described by Eqs. (2) and (3), where f is the frequency and D is the average diameter of a particle (Ultrasound Technology Compendium, pp. 946 to 951, published by Nikkan Kogyo Shinbunsha, Dec. 1, 1980).

$$\alpha = A f^4 D^3: \text{ wavelength } \lambda > 2\pi D \text{ (Rayleigh scattering)} \quad (2)$$

$$\alpha = B f^2 D: \lambda < 2\pi D \text{ (Stochastic scattering)} \quad (3)$$

where A and B are proportional coefficients.

The scattering attenuation for gas cavities is similar in that the energy of high frequency components in comparison with that of low frequency components attenuates at a short distance; and as the propagation distance increases, the low frequency components become dominant. That is, there is a correlation relationship between the propagation distance and the frequency components of ultrasonic waves after propagation. Hence, by obtaining this correlation relationship beforehand, a distance of propagation can be measured inversely from the frequency components for the same material.

Figure 6:
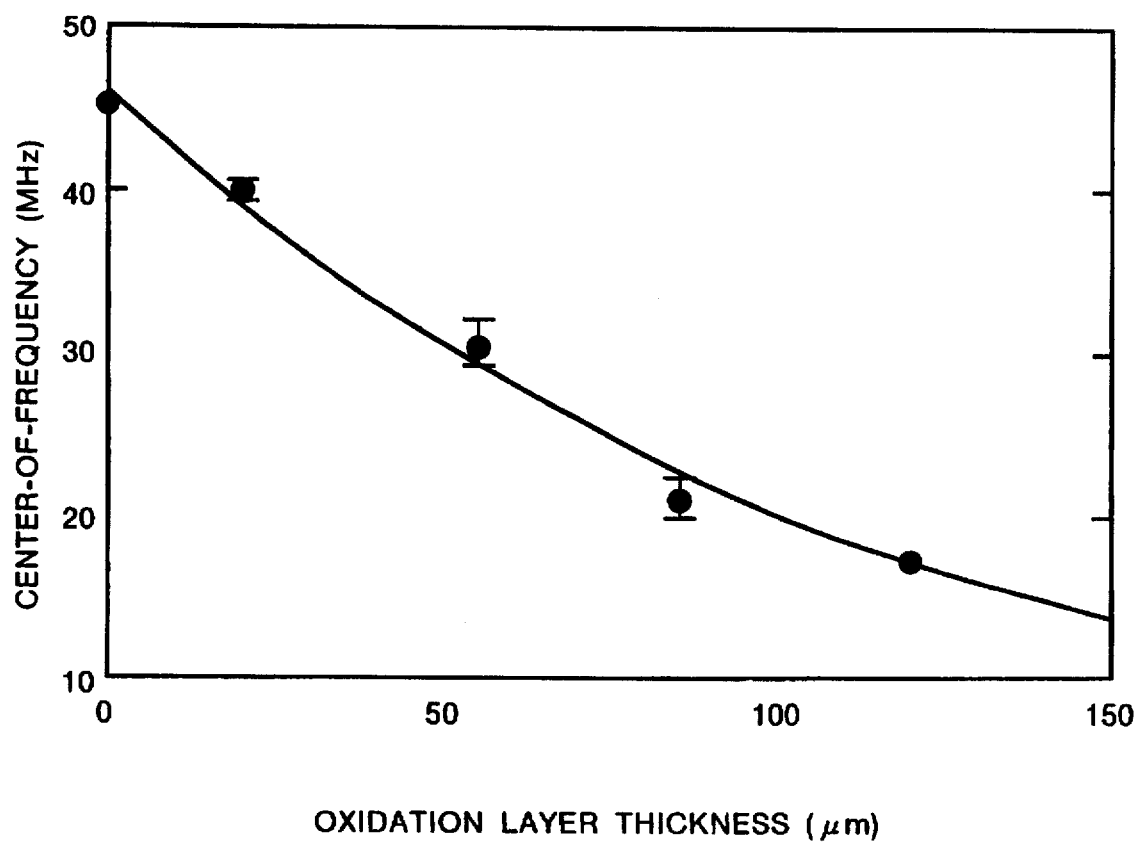
FIG. 6 is a descriptive diagram of changes of a center-of-frequency of reflection waves with respect to an oxidation layer thickness.

In the present embodiment, as shown in FIG. 1, because the bottom surface echo reflected at the bottom surface of the tube 10 is analyzed, the frequency spectrum receives correctly the influence of thickness of both the base metal and the oxidation layer. However, in this case, the thickness of the base metal can be ignored, and a correlation relationship between the oxidation layer thickness and the frequency components can be approximated. The reason for this is as follows. The oxidation layer in comparison with the base metal has more gas cavities and cracks, which induce large acoustic characteristic changes. From this, it is obvious that the oxidation layer becomes dominant in scattering attenuation. Therefore, the changes in the frequency spectrum are thought to arise almost all from the influence of the oxidation layer. When the center-of-frequency is calculated from the frequency spectrum of FIG. 5, the center-of-frequency shifts toward a lower frequency together with the increase in the oxidation layer thickness, as shown in FIG. 6.

Figure 7:
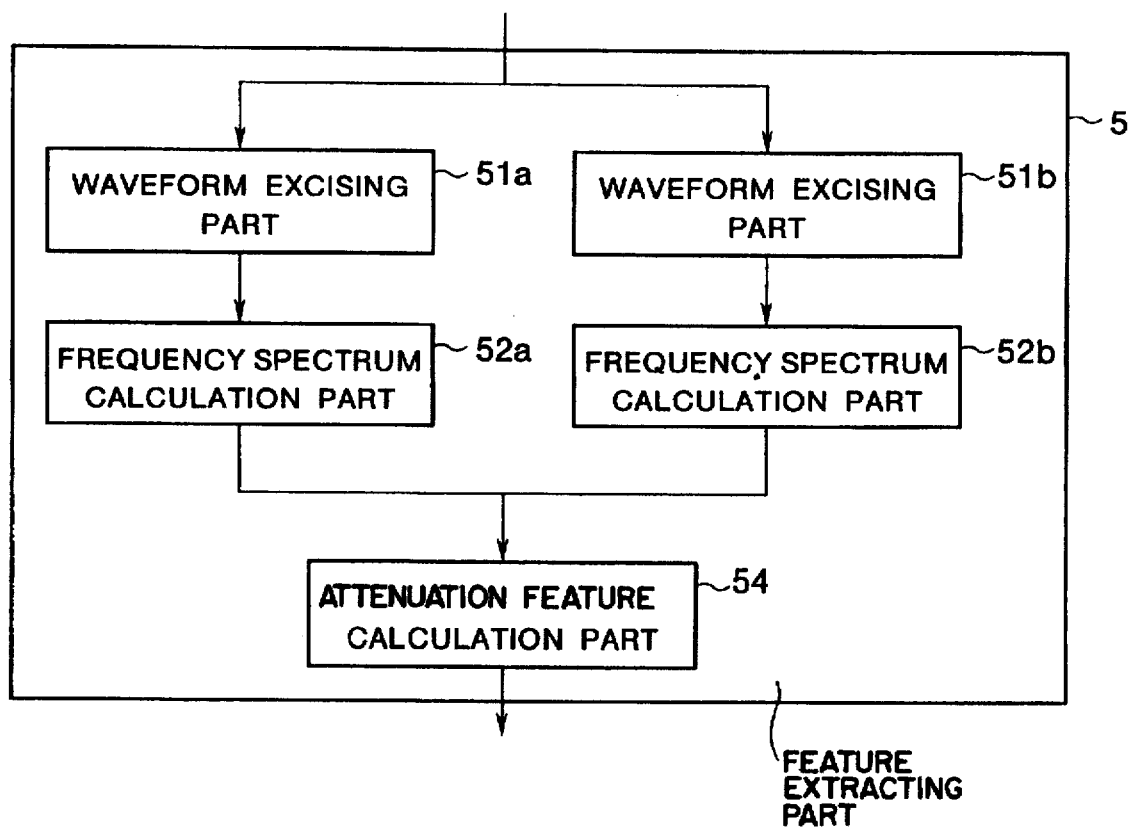
FIG. 7 shows a block diagram of another example of a signal feature extracting part of FIG. 1.

Next, a concrete structural example of a second example of the feature extracting part 5 is explained in reference to FIG. 7. A structure that leads from a waveform excising part 51a to a frequency spectrum calculation part 52a and a structure that leads from a waveform excising part 51b to a frequency spectrum calculation part 52b are the same as the structure that leads from the waveform excising part 51 to the frequency spectrum calculation part 52 shown in FIG. 2. From these structures, first, a certain wave group as one unit is excised as a waveform by the waveform excising part 51a, in consideration of the bottom surface echo and the surface reflection echo. Additionally, in the waveform excising part 51b, a certain wave group that has propagated through the oxidation layer 11, that is, in regard to the positioning of the present embodiment, a group of bottom surface echoes as one unit is excised as a waveform. For example, the first bottom surface echo is excised by the waveform excising part 51a, and the second bottom surface echo is excised by the waveform excising part 51b. Next, frequency spectra g1(f) and g2(f) for respective excised waveforms are calculated respectively by the frequency spectrum calculation parts 52a and 52b. Since the first bottom surface echo has passed the oxidation layer in one round trip, and the second bottom surface echo has passed the oxidation layer in two round trips, the frequency components for each of the waveforms differ by the reason stated above. Hence, by comparing the two waveforms, a propagation route having the propagation route of the second bottom surface echo subtracted from the propagation route of the first bottom surface echo can be calculated, and hence, an attenuation feature of the propagation route of one round trip can also be derived. This can be used as a signal feature data.

Next, at an attenuation feature calculation part 54, an attenuation feature A(f) between the two frequency spectra g1(f) and g2(f) is determined. This is approximated to an n-th order curve $a + b \cdot f^n$ (n is a positive real number), and an n-th order coefficient b is determined as a signal feature. The attenuation feature A(f) is shown as Eq. (4).

$$A(f) = 20 \log(g1(f)/g2(f)) \quad (4)$$

The spectra g1(f) and g2(f) obtained by changing the transmission and reflection rates by using differing contact mediums become $\alpha \cdot g1(f)$ and $\beta \cdot g2(f)$, where $\alpha$ and $\beta$ are real number coefficients, and for the attenuation feature A(f) at this point, the constant, a, changes but the n-th order coefficient, b, does not. That is, the n-th order coefficient, b, of the attenuation feature A(f) is not influenced by changes in the transmission and reflection rates.

Furthermore, in this structural example, even if the frequency spectrum distribution of ultrasonic waves are propagated from the ultrasound transmit device 2 to the tube 10 under the influence of the probe condition and such, there is an effect that error in thickness evaluation results are not readily produced because the ratio of g1(f) and g2(f) is taken, as shown in Eq. (4), to cancel out the influence.

Figure 8:
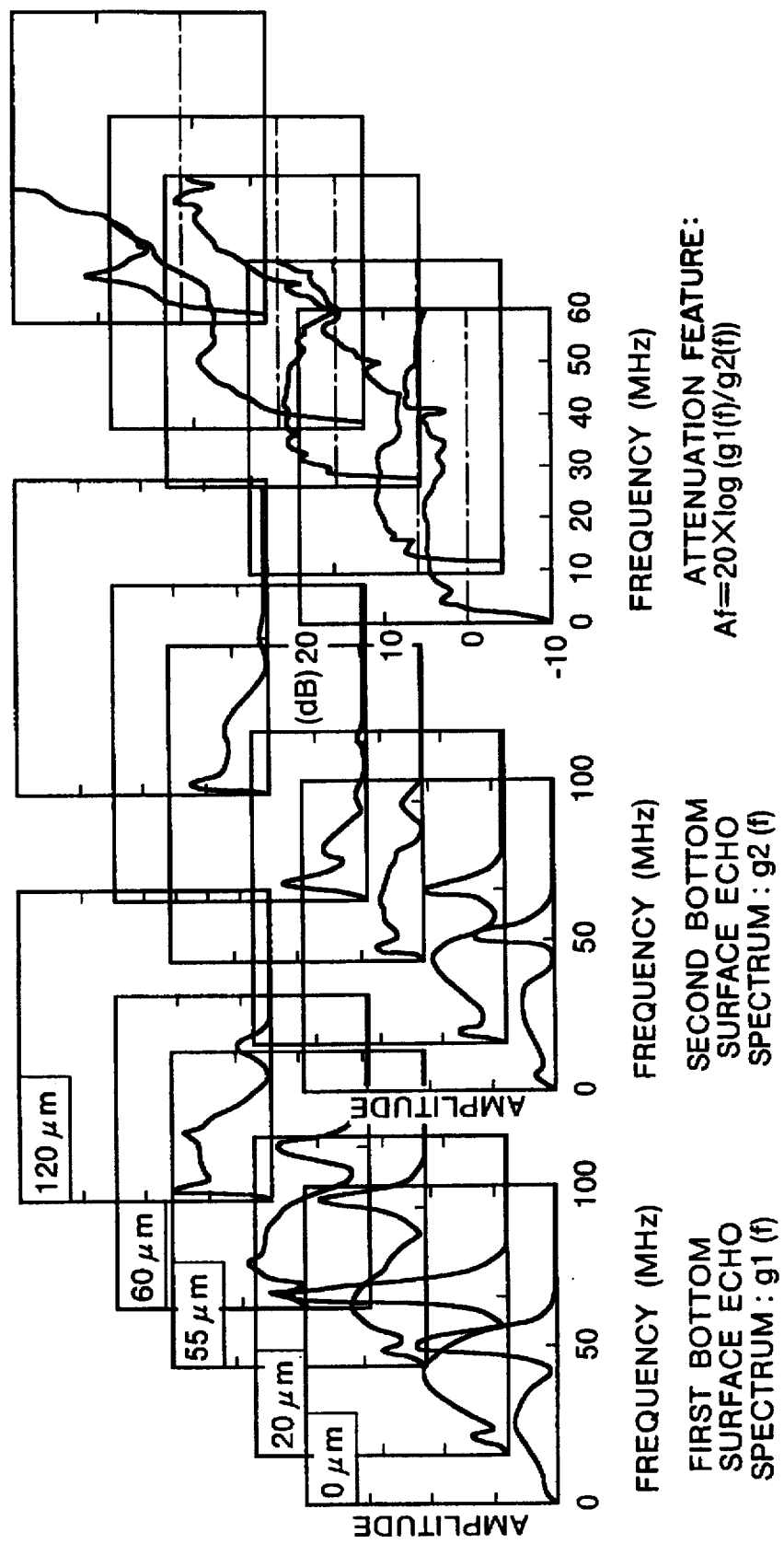
FIG. 8 is a descriptive diagram of a frequency spectrum of bottom surface echoes at each oxidation layer thickness and its attenuation feature.
Figure 9:
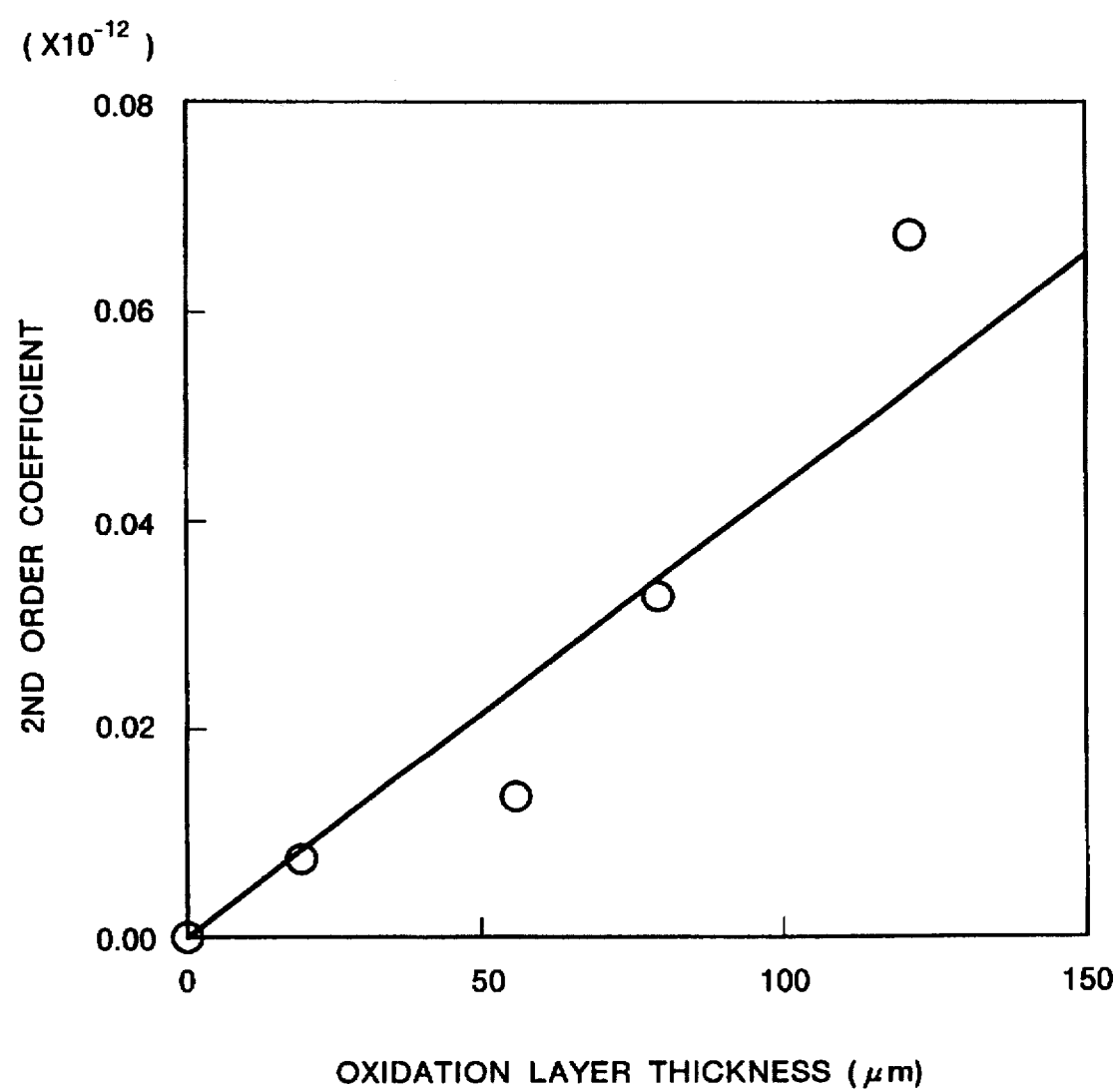
FIG. 9 is a descriptive diagram of changes of a 2nd order coefficient of a 2nd order curve of an attenuation feature with respect to an oxidation layer thickness.

An example of the attenuation feature A(f) with respect to the oxidation layer thickness obtained by the apparatus structure of FIG. 1 is indicated in FIG. 8, and a condition of the change of a layer thickness with respect to the 2nd order coefficient, b, of a 2nd order curve approximated to the attenuation feature A(f) is indicated in FIG. 9.

Figure 10:
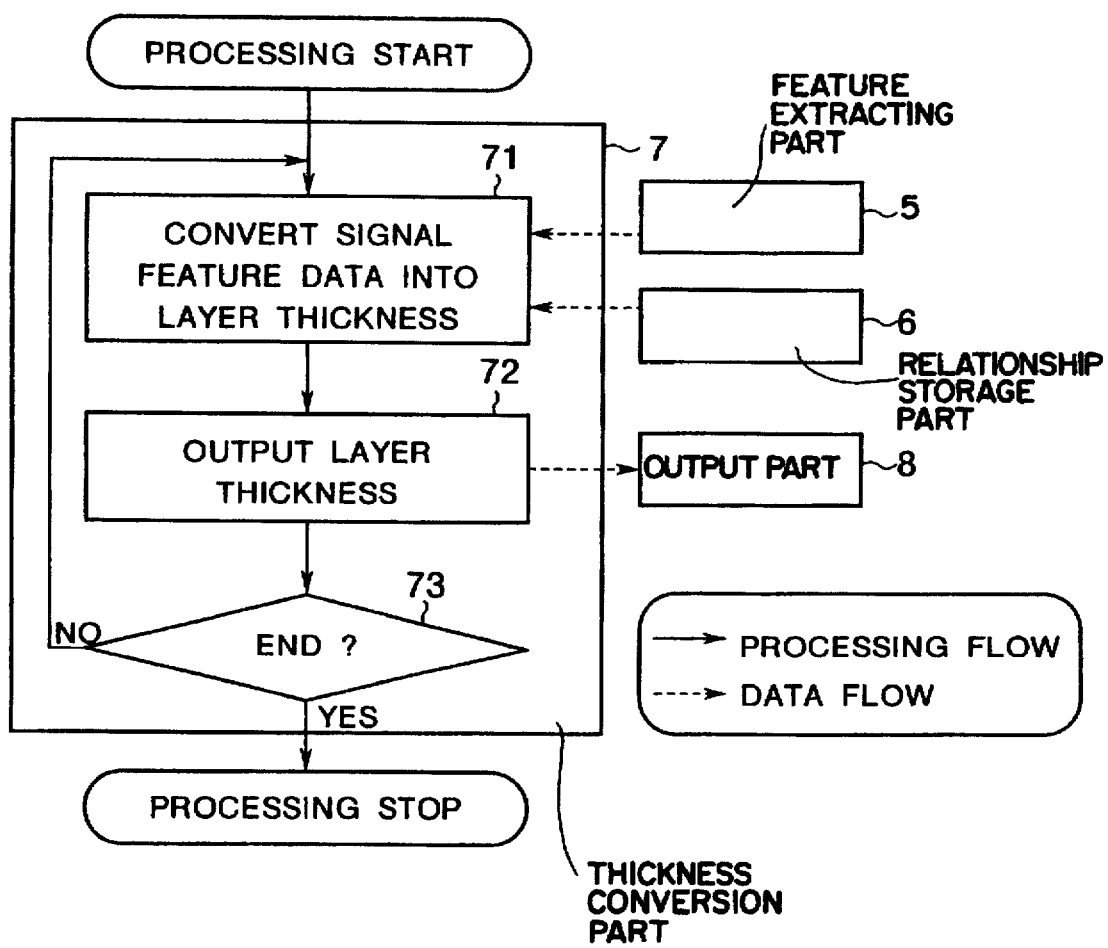
FIG. 10 shows a block diagram of a processing example of a thickness conversion part of FIG. 1.

Next, an example of a process performed by the thickness conversion part 7 is explained. In FIG. 10, a relationship between the thickness conversion part 7 and data flow is shown. After processing has started, Yr, a measurement data of the signal feature, is read in from the signal feature extracting part 5 at step 71. And a relationship (X(k), Y(k)) (k=1~m, where m is the total data number) between Y(k), a reference data of the signal feature, and X(k), the layer thickness, is read in from the relationship storage part 6.

From this thickness function, the measurement data of the signal feature is converted into a certain thickness. It should be mentioned that the measurement data of the signal feature Yr is either the center-of-frequency, fm, of the frequency spectrum or an n-th order (n is a positive real number) coefficient of an attenuation among a plurality of frequency spectra. At step 72, the layer thickness is outputted to the output part 8, and at step 73, whether the processing is finished or not is determined, and if it is not finished, the process returns to step 71.

Figure 11:
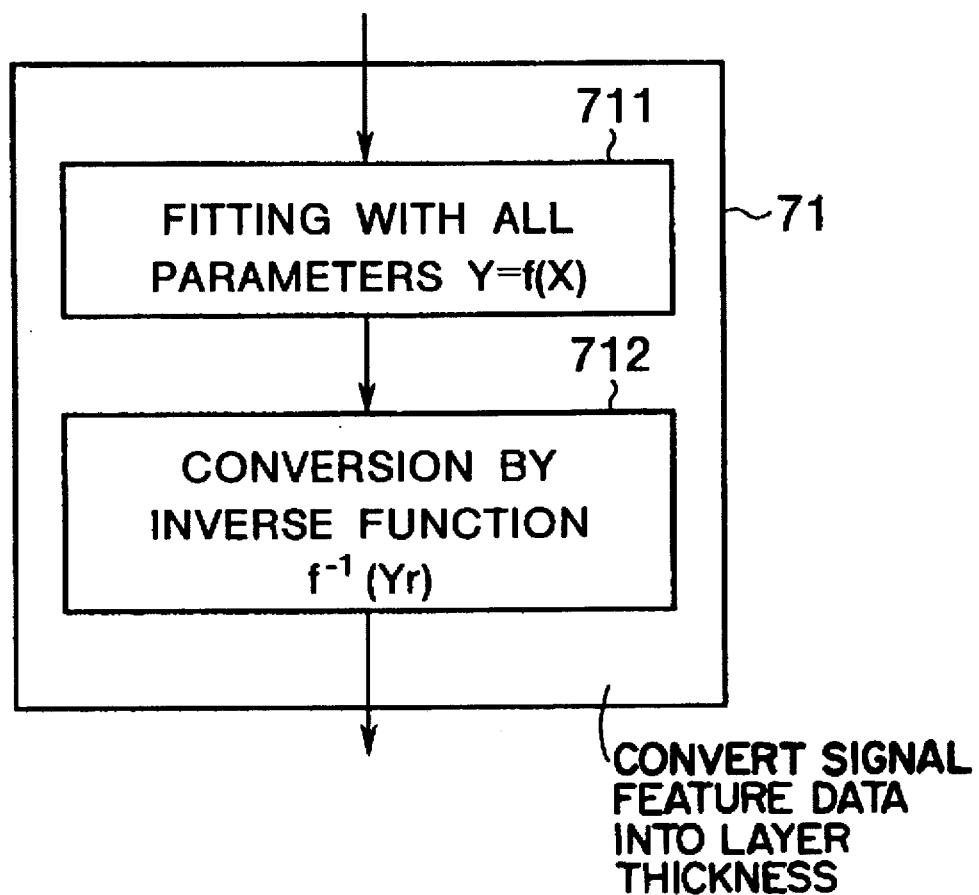
FIG. 11 shows a flow chart of an example of a process for converting a signal feature into the thickness of an object.

A processing example step 71 is shown in FIG. 11. First, concerning the entire relationship of the layer thickness X(k) read in and the measurement data of the signal feature Y(k), curve fitting by an exponential function and such is performed at step 711, that is, a functional approximation is applied. And, therefore, a relationship between the thickness of the oxidation layer 11 and the measurement data of the signal feature, Y=f(X), is obtained. At step 712, by inserting the measurement data Yr into an inverse function, $f^{-1}(Yr)$, Yr is converted into a layer thickness.

Figure 12:
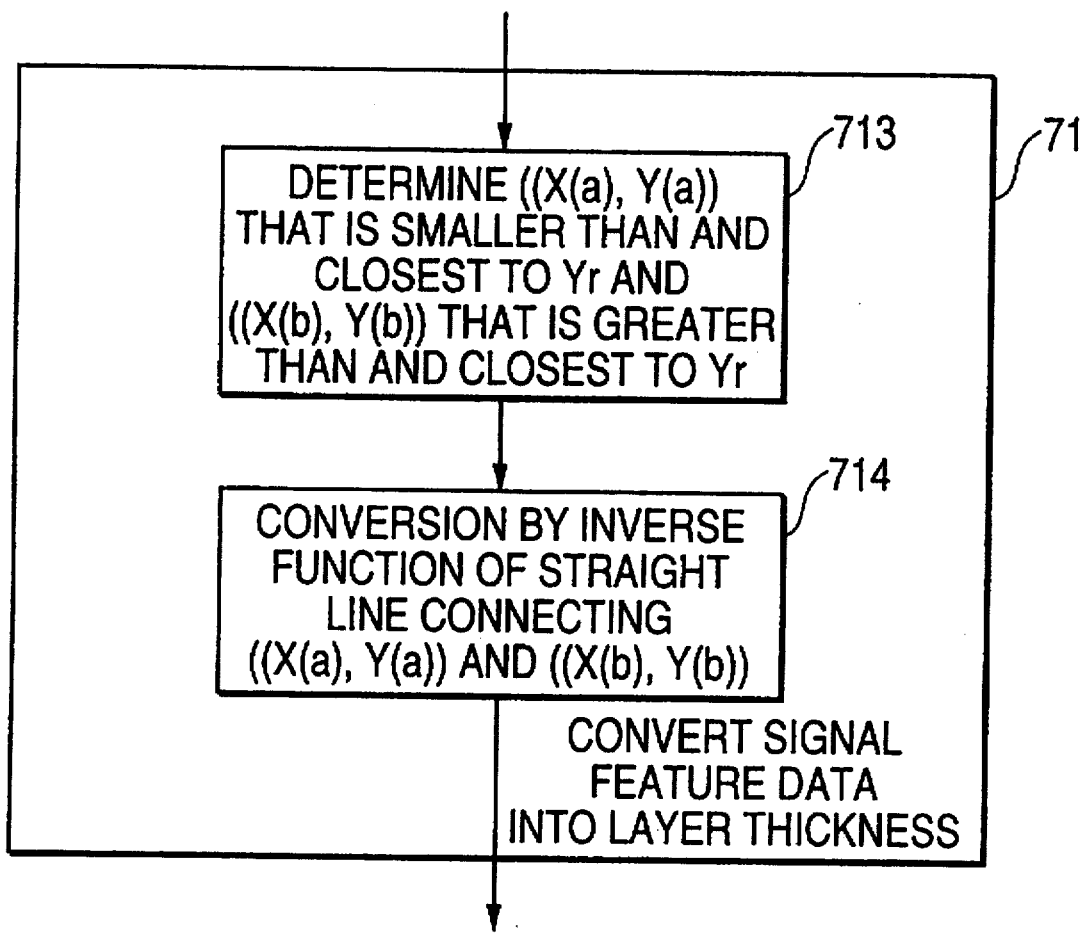
FIG. 12 shows a flow chart of another example of a process for converting a signal feature into the thickness of an object.

Furthermore, there is a processing method shown in FIG. 12 as an alternative to the processing example of step 71. First, at step 713, (X(a), Y(a)) that is smaller than and closest to the measurement data Yr read in and (X(b), Y(b)) that is greater than and closest to the measurement data Yr are determined. At step 714, a straight line that connects these two points is determined, and by substituting Yr into an inverse function of this, a layer thickness conversion takes place.

Figure 13:
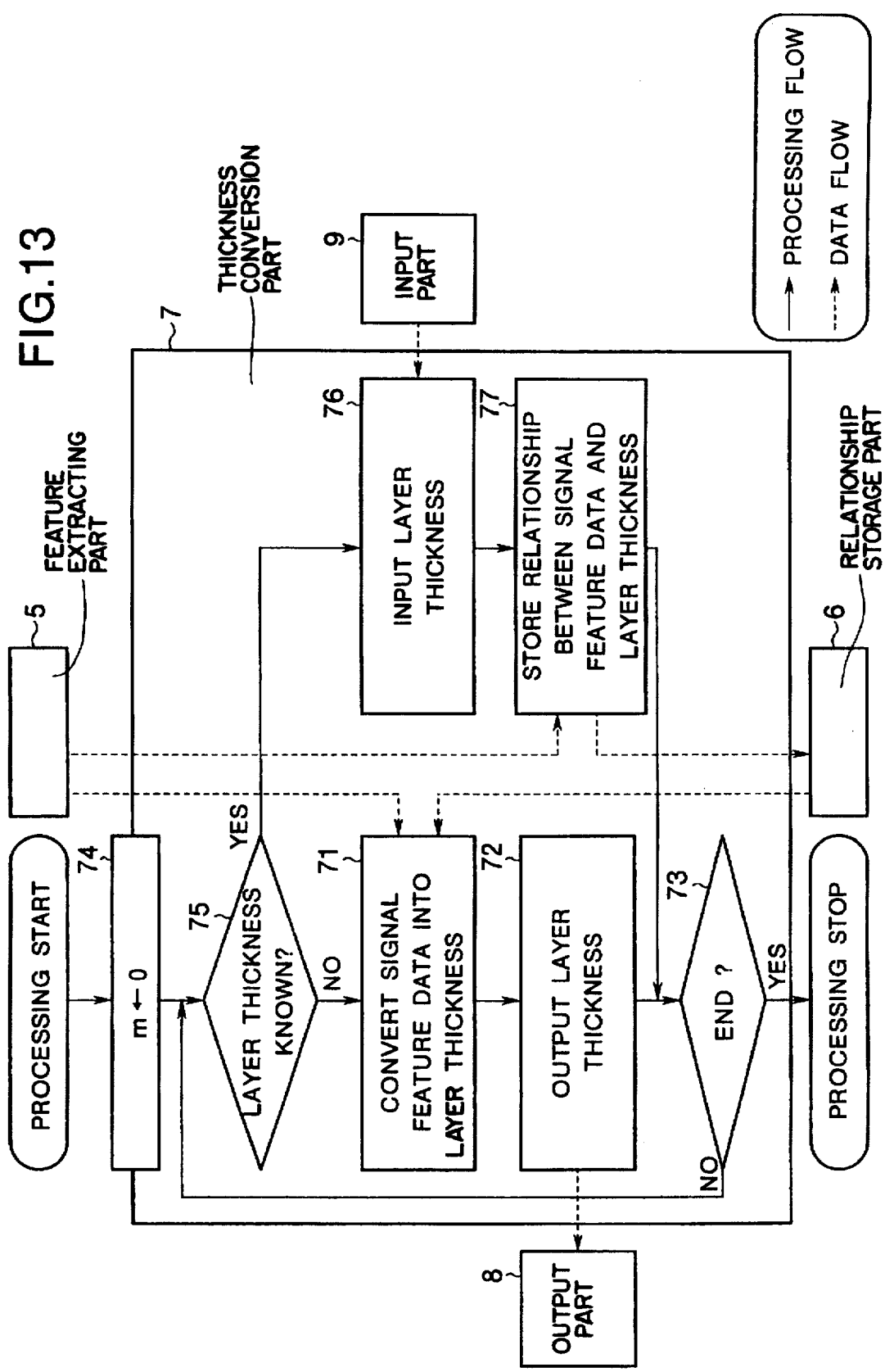
FIG. 13 shows a flow chart of a content of a process of a thickness conversion part.

Next, a concrete example of a process in which the thickness conversion part 7 has a function to store the thickness function into the relationship storage part 6 is shown in FIG. 13. After processing has started, at step 74, m, the total number of the functional data of the thickness function that describes the relationship between the layer thickness and the signal feature data stored in the relationship storage part 6, is set to zero. At step 75, whether the layer thickness is known or not is determined. If the thickness of the oxidation layer is known at the time of measurement, the layer thickness is read in from the input part 9 at step 76.

Next at step 77, the signal feature data obtained from a measurement result from the signal feature extracting part 5 is read in, and the relationship between the layer thickness and the signal feature data at the time of measurement is stored in the relationship storage part 6. At step 73, whether the processing has been completed or not is determined, and if it has not been completed, the process returns to step 75. On the other hand, at step 75, if the layer thickness is unknown, the same process as in FIG. 10 is performed.

Figure 14:
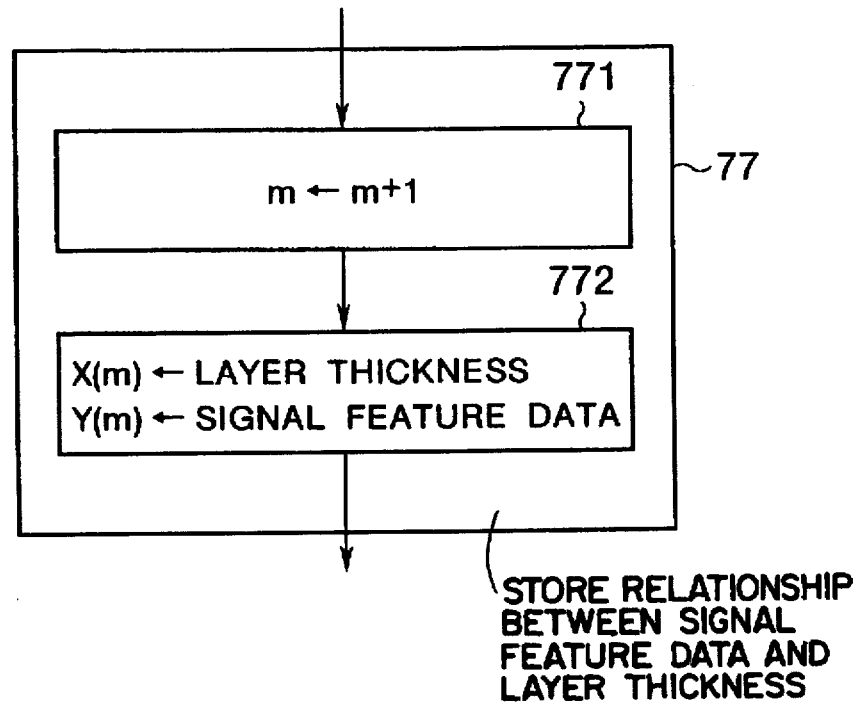
FIG. 14 shows a flow chart of a process that records a relationship between the thickness of an object and the signal feature.

A flow chart of a processing example of step 77 is shown in FIG. 14. In step 771, the value, m, is incremented by one. Next, at step 772, the thickness of the oxidation layer 11 is inserted into X(m) and the signal feature data is inserted into Y(m).

In the embodiment of the thickness conversion part 7 above, with respect to the thickness of the oxidation layer 11, the signal feature data of only one variable was used, but a signal feature data with more than one variable may be used as well. In this instance, the conversion of the thickness of the oxidation layer 11 may be performed by selecting only one variable at the time of measurement or by defining a conversion method for a plurality of variables.

Figure 15:
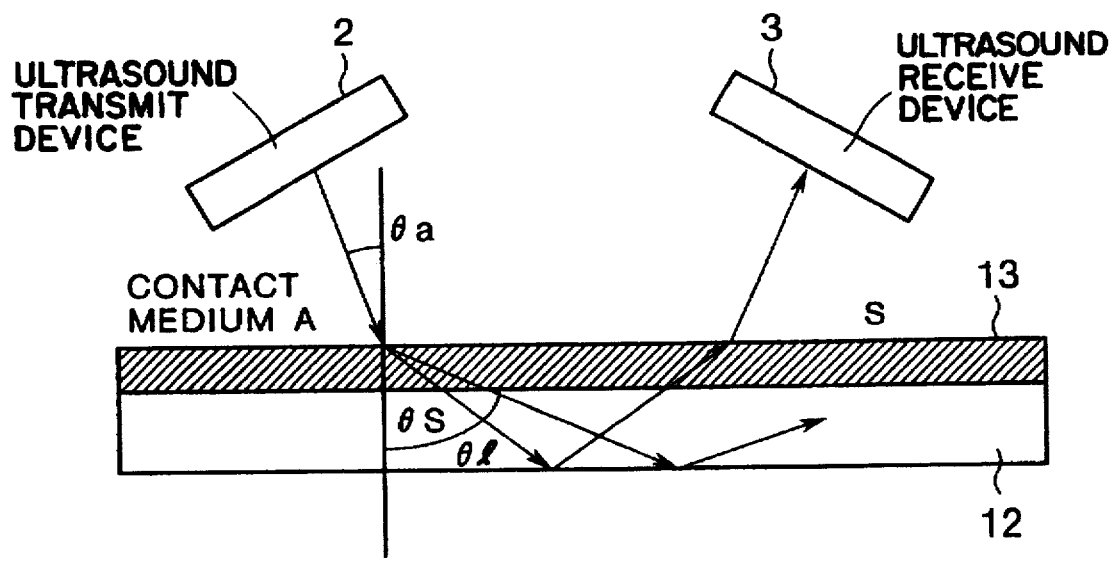
FIG. 15 is a descriptive diagram of an example of an apparatus of a transmit device that transmits shear waves and a receive device that receives these waves.

A case in which the ultrasound transmit device 2 of FIG. 1 produces a shear wave in an object 12 and the ultrasound receive device 3 receives this shear wave is shown in FIG. 15. The beam axis of the ultrasound transmit device 2 and the beam axis of the ultrasound receive device 3 are set at an angle so as to obliquely intersect with the object 12. A longitudinal wave transmitted from the ultrasound transmit device 2 refracts at the surface S of the object, and is mode converted into a longitudinal wave and a shear wave. A refraction angle for each wave is determined by Snell's law of Eq. (5).

$$\sin\theta a/Va = \sin\theta 1/V1 = \sin\theta s/Vs \qquad (5)$$

where θa is the incident angle, Va is the longitudinal wave acoustic velocity in the contact medium A, θ1 is the refraction angle of the longitudinal wave at the surface S of the object 12, V1 is the longitudinal wave acoustic velocity in the object 12, θs is the refraction angle of the shear wave at the surface S of the object 12, and Vs is the shear wave acoustic velocity in the object 12. A difference of acoustic velocity at a layer 13 of the object 12 and at a point other than the layer 13 is assumed to be negligibly small so that it can be disregarded.

Figure 16:
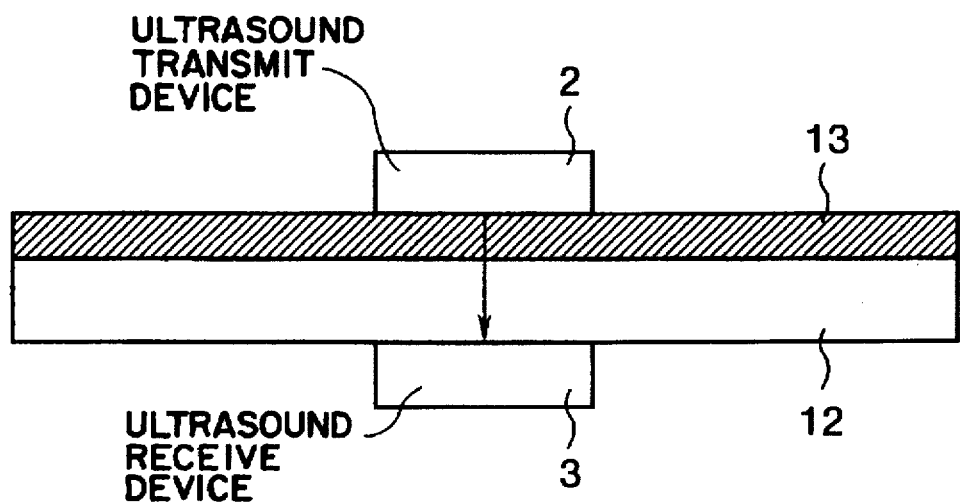
FIG. 16 is a descriptive diagram of another example of an apparatus of a transmit device that transmits shear waves and a receive device that receives these waves.

From the above equation, the incident angle θa at which the shear wave will be produced may be determined. Furthermore, if an interference between the shear wave and the longitudinal wave is not desired, the incident angle θa should be set to an angle at which only the shear wave propagates inside the object 12. A measurement that uses the shear wave can be realized also by a structural example as shown by a descriptive diagram in FIG. 16. In this instance, the ultrasound transmit device 2 utilizes a mechanism that directly generates the shear wave. The advantage of the shear wave is that generally the attenuation is larger than that of the longitudinal wave (Ultrasound Experimental Technology—Theory and Reality, p. 97, Japan Nohritsu Kyokai, Feb. 25, 1980). Consequently, the center-of-frequency has a larger change in the attenuation feature, and a measurement with good sensitivity can be achieved even for a very thin layer.

Figure 17:
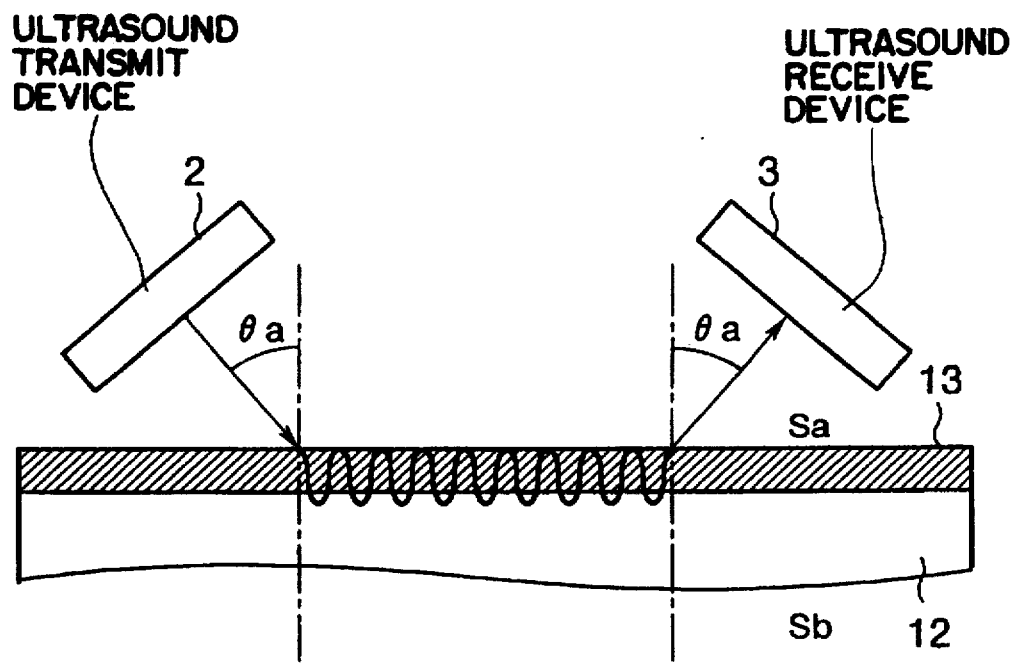
FIG. 17 is a descriptive diagram of an example of a transmit device that transmits surface acoustic waves and a receive device that receives these waves.

A structural example in which the ultrasound transmit device 2 of FIG. 1 produces a surface acoustic wave in the object and the ultrasound receive device 3 receives this surface acoustic wave is shown in FIG. 17. The set angle θa of a beam axis of the ultrasound transmit device 2 and a beam axis of the ultrasound receive device 3 is given by Snell's law of Eq. (6).

$$\sin\theta a/Va = 1/Vr \qquad (6)$$

where θa is the incident angle, Va is the longitudinal wave acoustic velocity in the contact medium A, and Vr is the acoustic velocity of the surface acoustic wave in the object 12. A difference of acoustic velocity at the layer 13 of the object 12 and at a point other than the layer 13 is assumed to be negligibly small so that it can be disregarded. Since the energy of the surface acoustic wave is mostly concentrated between the front surface Sa of the object 12 and a depth of one wavelength, there is a correlation between the thickness of the layer 13 and the attenuation. From this, it becomes possible to measure the layer thickness by using the surface acoustic wave. Furthermore, a measurement involving the surface acoustic wave carries the effect of not being influenced by the back surface Sb of the object 12.

Figure 18:
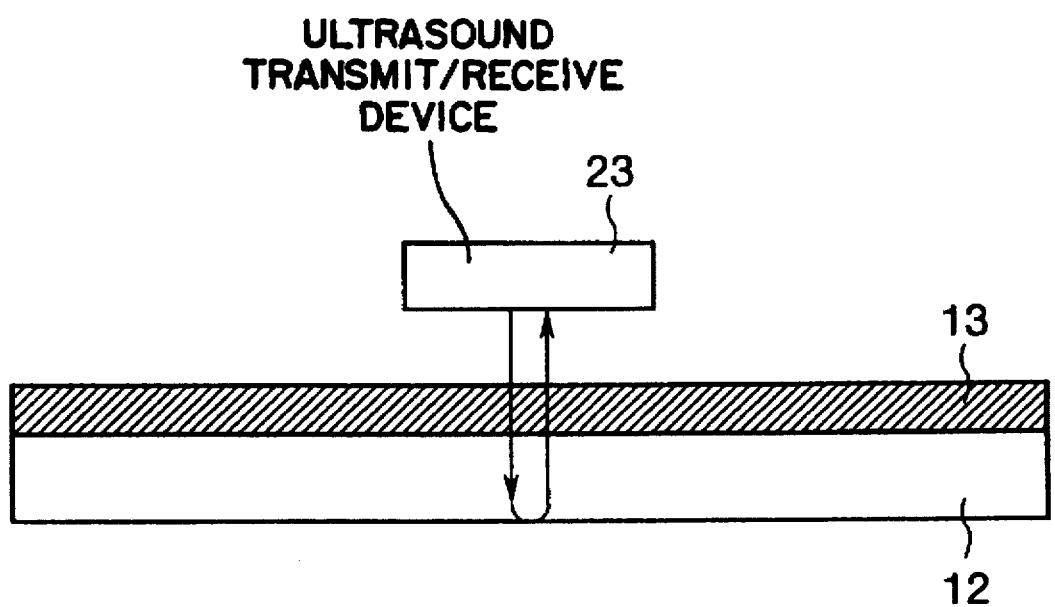
FIG. 18 is a descriptive diagram of an example of a transmit/receive device that serves to receive and transmit.

In the above embodiment, the ultrasound transmit device 2 has the transmitting function and the ultrasound receive device 3 has the receiving function, but, as shown in FIG. 18, in an ultrasound transmit/receive device 23, both of the transmitting and receiving functions are combined in one device. Even in this instance, the layer thickness can be measured by the apparatus as described above.

Figure 19:
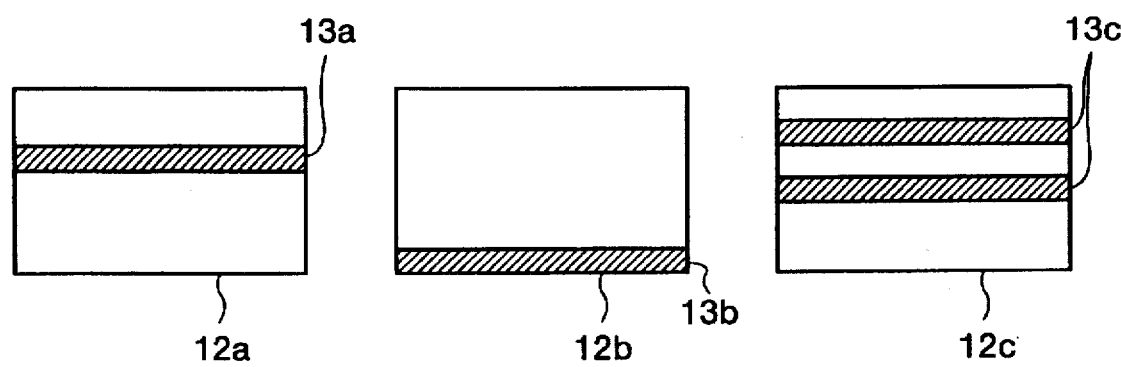
FIG. 19 is a descriptive diagram of an example of an object that can be measured.

As shown in FIG. 19, a layer of an object that is the subject for measurement can be measured by the same method and apparatus even a layer 13a is formed inside an object 12a or a layer 13b is formed on the back side of an object 12b. However, a measurement with the surface acoustic wave requires a layer formation that propagates the surface acoustic wave. Furthermore, multiple layer 13c in an object 12c can be measured if the layers are of the same type. In this instance, the total thickness of the layers 13c can be measured. Furthermore, the whole object may be the subject for measurement. That is, the same apparatus can be used to measure simply the wall thickness of the object.

According to the present invention, since a received signal is converted into a frequency spectrum, not only the overall signal amplitude but also the amplitude distribution with respect to frequency can be known. In this respect, when there is a change in the amplitude distribution in addition to the amplitude change of the signal in accordance with the thickness of the subject-to-measurement part, it would be also possible to measure the thickness by the evaluation of relative amplitudes. With regard to this, there is an effect that an estimation error is not produced even when sound reflection and transmission rates change in accordance with an apparent attenuation which does change the signal amplitude but not the relative amplitudes—an apparent attenuation which occurs, for example, when a contact medium during measurement is different from a contact medium used at the relationship storage time when a relationship between received waves and the thickness of an object to be measured was obtained.

Further, according to the present invention, since the center-of-frequency of the frequency spectrum, which is an integration information, is made to be the signal feature data of the receive signals, there is an effect that it is not susceptible to the influence of white-noise-like strength changes attributed to the interferences of waveforms due to multiple reflections.

Still further, according to the present invention, since the coefficient b of the n-th order of attenuation among a plurality of frequency spectra is made to be the signal feature data, there is an effect that the frequency spectrum distribution obtained before the ultrasonic waves are transmitted into the object to be measured is not easily influenced by an apparent attenuation that occurs when a contact medium used during measurement is different from a contact medium used at the relationship storage time.

Still further, according to the present invention, since a shear wave, which has a greater attenuation in comparison with that of a longitudinal wave, is used, the fluctuation of the signal feature data is large. Consequently, there is an effect that it has a high sensitivity even for a very thin object subject to measurement.

Still further, according to the present invention, since a surface acoustic wave that propagates near the front surface of the object for measurement is utilized, a measurement can be made without being influenced by the condition of the back surface of the object to be measured.

What is claimed is:

1. A method for measuring a thickness of a layer on a front surface of a test object using acoustic waves, the method comprising the steps of:

transmitting respective acoustic waves to a plurality of reference objects having respective front surfaces with respective layers thereon, the layers of the reference objects being of a same type as the layer of the test object and having respective known mutually different thicknesses;

receiving respective acoustic waves from the reference objects, the acoustic waves received from the reference objects having been produced by the acoustic waves transmitted to the reference objects and being one of (1) reflected acoustic waves which have passed through the reference objects and have been reflected from respective back surfaces of the reference objects at least once, and (2) transmitted acoustic waves which have passed through the reference objects at least once;

determining respective frequency spectrums of the acoustic waves received from the reference objects;

determining respective centers-of-frequency of the frequency spectrums of the acoustic waves received from the reference objects;

determining a thickness function defining a relationship between the centers-of-frequency of the frequency spectrums of the acoustic waves received from the reference objects and the thicknesses of the layers of the reference objects;

transmitting an acoustic wave to the test object;

receiving an acoustic wave from the test object, the acoustic wave received from the test object having been produced by the acoustic wave transmitted to the test object and being one of (1) a reflected acoustic wave which has passed through the test object and has been reflected from a back surface of the test object at least once, and (2) a transmitted acoustic wave which has passed through the test object at least once;

determining a frequency spectrum of the acoustic wave received from the test object;

determining a center-of-frequency of the frequency spectrum of the acoustic wave received from the test object; and determining the thickness of the layer of the test object from the thickness function based on the center-of-frequency of the frequency spectrum of the acoustic wave received from the test object.

2. A method for measuring a thickness of a layer on a front surface of a test object using acoustic waves, the method comprising the steps of:

transmitting respective acoustic waves to a plurality of reference objects having respective front surfaces with respective layers thereon, the layers of the reference objects being of a same type as the layer of the test object and having respective known mutually different thicknesses;

receiving respective first acoustic waves and respective second acoustic waves from the reference objects, the first acoustic waves and the second acoustic waves received from the reference objects having been produced by the acoustic waves transmitted to the reference objects and being one of (1) reflected acoustic waves which have passed through the reference objects and have been reflected from respective back surfaces of the reference objects at least once, and (2) transmitted acoustic waves which have passed through the reference objects at least once, the second acoustic waves received from the reference objects having passed through the reference objects a greater number of times than the first acoustic waves received from the reference objects;

determining respective frequency spectrums of the first acoustic waves and the second acoustic waves received from the reference objects;

determining respective attenuation features for the reference objects, the attenuation features for the reference objects being determined between the frequency spectrums of the first acoustic waves received from the reference objects and the frequency spectrum of the second acoustic waves received from the reference objects, the attenuation features for the reference objects being approximated by an attenuation feature function having a coefficient, a value of the coefficient of the attenuation feature function being different for each of the attenuation features for the reference objects;

determining respective values of the coefficient of the attenuation feature function for the attenuation features for the reference objects;

determining a thickness function defining a relationship between the values of the coefficient of the attenuation feature function for the attenuation features for the reference objects and the thicknesses of the layers of the reference objects;

transmitting an acoustic wave to the test object;

receiving a first acoustic wave and a second acoustic wave from the test object, the first acoustic wave and the second acoustic wave received from the test object having been produced by the acoustic wave transmitted to the test object and being one of (1) a reflected acoustic wave which has passed through the test object and has been reflected from a back surface of the test object at least once, and (2) a transmitted acoustic wave which has passed through the test object at least once, the second acoustic wave received from the test object having passed through the test object a greater number of times than the first acoustic wave received from the test object;

determining respective frequency spectrums of the first acoustic wave and the second acoustic wave received from the test object;

determining an attenuation feature for the test object, the attenuation feature for the test object being determined between the frequency spectrum of the first acoustic wave received from the test object and the frequency spectrum of the second acoustic wave received from the test object;

determining a value of the coefficient of the attenuation feature function for the attenuation feature for the test object; and determining the thickness of the layer of the test object from the thickness function based on the value of the coefficient of the attenuation feature function for the attenuation feature for the test object.

3. An apparatus for measuring a thickness of a layer on a surface of a test object using acoustic waves, the apparatus comprising:

acoustic wave transmitting/receiving means for transmitting an acoustic wave to the test object from a first position, receiving an acoustic wave from the test object at a second position different from the first position, the acoustic wave received from the test object having been produced by the acoustic wave transmitted to the test object and having passed through the test object at least once, and outputting an acoustic wave signal indicative of the acoustic wave received from the test object;

waveform extracting means for extracting a waveform from the acoustic wave signal outputted by the acoustic wave transmitting/receiving means;

frequency spectrum calculating means for calculating a frequency spectrum of the waveform extracted by the waveform extracting means;

center-of-frequency calculating means for calculating a center-of-frequency of the frequency spectrum calculated by the frequency spectrum calculating means;

thickness function storing means for storing a predetermined thickness function defining a relationship between the center-of-frequency calculated by the center-of-frequency calculating means and the thickness of the layer of the test object;

thickness converting means for converting the center-of-frequency calculated by the center-of-frequency calculating means into the thickness of the layer of the test object based on the predetermined thickness function stored in the thickness function storing means; and output means for outputting the thickness of the layer of the test object obtained by the thickness converting means.

4. An apparatus according to claim 3, wherein the acoustic wave transmitting/receiving means includes:

means for producing a shear wave in the layer of the test object; and means for receiving a shear wave that has propagated through the layer of the test object.

5. An apparatus according to claim 3, wherein the acoustic wave transmitting/receiving means includes:

means for producing a surface acoustic wave in the layer of the test object; and means for receiving a surface acoustic wave that has propagated through the layer of the test object.

6. An apparatus for measuring a thickness of a layer on a surface of a test object using acoustic waves, the apparatus comprising:

acoustic wave transmitting/receiving means for transmitting an acoustic wave to the test object from a first position, receiving a first acoustic wave and a second acoustic wave from the test object at a second position different from the first position, the first acoustic wave and the second acoustic wave received from the test object having been produced by the acoustic wave transmitted to the test object and having passed through the test object at least once, the second acoustic wave received from the test object having passed through the test object a greater number of times than the first acoustic wave received from the test object, and outputting a first acoustic wave signal indicative of the first acoustic wave received from the test object and a second acoustic wave signal indicative of the second acoustic wave received from the test object;

waveform extracting means for extracting a first waveform from the first acoustic wave signal outputted by the acoustic wave transmitting/receiving means and a second waveform from the second acoustic wave signal outputted by the acoustic wave transmitting/receiving means;

frequency spectrum calculating means for calculating a first frequency spectrum of the first waveform extracted by the waveform extracting means and a second frequency spectrum of the second waveform extracted by the waveform extracting means;

attenuation feature calculating means for calculating an attenuation feature between the first frequency spectrum calculated by the frequency spectrum calculating means and the second frequency spectrum calculated by the frequency spectrum calculating means, the attenuation feature being approximated by an attenuation feature function having a coefficient, and calculating a value of the coefficient of the attenuation feature function;

thickness function storing means for storing a predetermined thickness function defining a relationship between the coefficient of the attenuation feature function calculated by the attenuation feature calculating means and the thickness of the layer of the test object;

thickness converting means for converting the coefficient of the attenuation feature function calculated by the attenuation feature calculating means into the thickness of the layer of the test object based on the predetermined thickness function stored in the thickness function storing means; and output means for outputting the thickness of the layer of the test object obtained by the thickness converting means.

7. An apparatus according to claim 6, wherein the acoustic wave transmitting/receiving means includes:

means for producing a shear wave in the layer of the test object; and means for receiving a shear wave that has propagated through the layer of the test object.

8. An apparatus according to claim 6, wherein the acoustic wave transmitting/receiving means includes:

means for producing a surface acoustic wave in the layer of the test object; and means for receiving a surface acoustic wave that has propagated through the layer of the test object.

* * * * *